United States Patent [19]

Liberti et al.

[11] Patent Number: 4,551,435
[45] Date of Patent: Nov. 5, 1985

[54] SELECTIVE REMOVAL OF IMMUNOSPECIFICALLY RECOGNIZABLE SUBSTANCES FROM SOLUTION

[75] Inventors: Paul A. Liberti, Churchville, Pa.; Paul Pollara, South Plainfield, N.J.

[73] Assignee: Immunicon, Inc., Philadelphia, Pa.

[21] Appl. No.: 526,039

[22] Filed: Aug. 24, 1983

[51] Int. Cl.$^4$ ............... G01N 33/54; B01D 27/00
[52] U.S. Cl. ............. 436/541; 210/348; 210/660; 210/927; 436/507; 436/509; 436/519; 436/531; 436/821; 604/5
[58] Field of Search ............. 436/512, 821, 507, 509, 436/519, 531, 541

[56] References Cited

U.S. PATENT DOCUMENTS

| | | | |
|---|---|---|---|
| 3,719,182 | 3/1973 | Rose | 605/5 X |
| 3,959,128 | 5/1976 | Harris | 604/5 X |
| 3,963,613 | 6/1976 | Chibata | 604/5 X |
| 4,143,124 | 3/1979 | Masson | 436/821 X |
| 4,332,783 | 6/1982 | Pernice | 436/512 X |

OTHER PUBLICATIONS

Asanuma, Y. et al., Tans. Am. Soc. Art. Intern. Organs, 26, 400, 1980.
Buffaloe, G., Trans. Am. Soc. Art. Intern. Organs, 27, 342, 1981.
Gurland, H. J. et al., Trans. Am. Soc. Art. Intern. Organs, 27, 356, 1981.
Jones, J. V. et al., Trans. Am. Soc. Art. Int. Organs, 27, 351, 1981.
Malchesky, P. S. et al., Artificial Organs, 4, 205, 1981.
Pineda, A. A. et al., Artificial Organs, 5, 234, 1981.
Randerson, D. H. et al., Artificial Organs, 6, 43, 1982.
Solomon, B. A., Trans. Am. Soc. Art. Intern. Organs, 27, 345, 1981.
Liberti, P. A. et al., Journal of Immunology, 123(5), 2212-2219, (1979).
"Manual of Clinical Immunology", N. R. Rose et al., eds., Chapt. 90, pp. 669-675, by V. Agnello, American Society for Microbiology, Washington, D.C., 1977.

*Primary Examiner*—Sidney Marantz
*Attorney, Agent, or Firm*—Dann, Dorfman, Herrell & Skillman

[57] ABSTRACT

A process and apparatus for removing immuno-specifically recognizable substances in the form of immune complexes from a solution. The solution containing preformed immune complexes or immune complexes already present therein is contacted with an adsorbent consisting of non-immunospecific factor such as Clq, rheumatoid factor, Fc receptor and Fc receptor-bearing cells.

20 Claims, 8 Drawing Figures

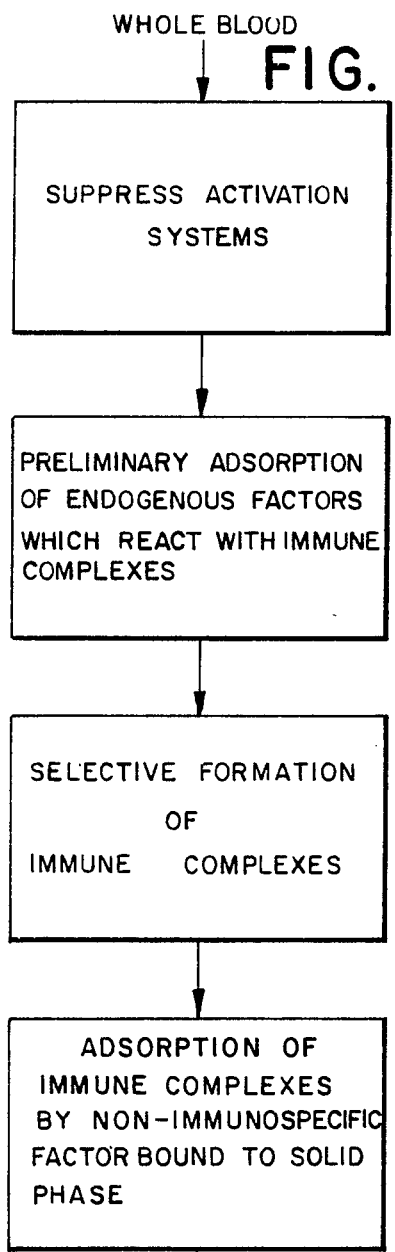
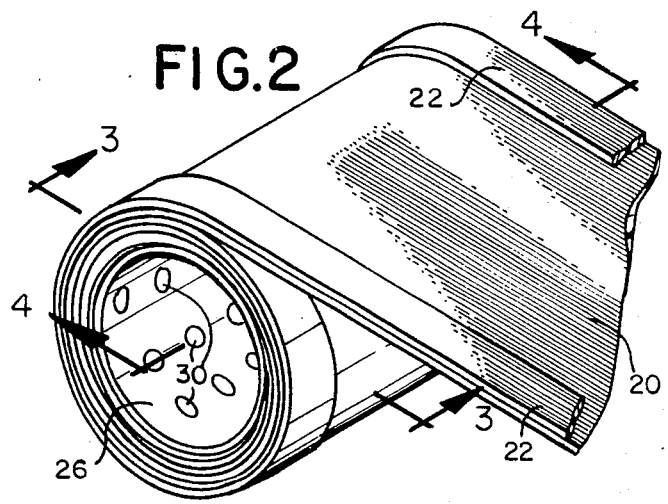
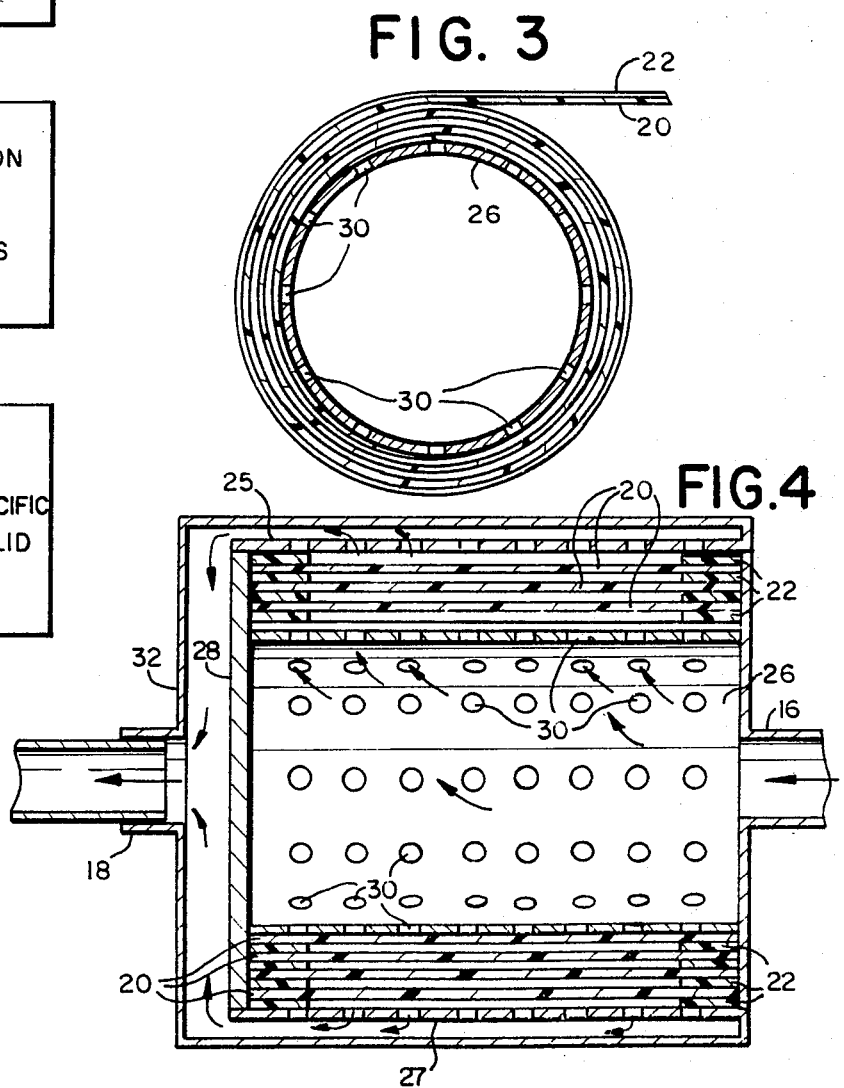

SELECTIVE REMOVAL OF IMMUNOSPECIFICALLY RECOGNIZABLE SUBSTANCES FROM SOLUTION

FIELD OF THE INVENTION

The present invention relates to a universal method and apparatus for immunospecifically removing from solution any soluble or suspended substance which can be immunospecifically recognized. The present invention has particular application to the removal of immunospecifically recognizable substances from biological fluids such as whole blood and bone marrow.

BACKGROUND OF THE INVENTION

Three different types of separation techniques are currently utilized in removing various substances from biological fluids such as blood. These separation techniques are based on different separation principles: (1) mechanical methods (density, size); (2) physical/chemical methods (solubility, electrical mobility); and (3) biological methods (substrate affinity, substrate reactivity).

With regard to mechanical techniques, centrifugal methods are commonly employed in various blood separator systems. Centrifugal methods are currently used in blood banking operations, and more recently for therapeutic plasma exchange. Filtration methods have also been employed for plasma separation and for differential filtration of plasma.

With regard to physical/chemical techniques, precipitation methods can be used employing reduced temperatures, i.e. in the separation of cryoglobulins. High ionic strength methods may also be used for the precipitation of globulins as in the case of the use of ammonium sulfate to precipitate immunoglobulins. Other additives, such as polyethylene glycol, can also be used for precipitation, in particular, the precipitation of immune complexes. An example of an electrical mobility method is the technique of forced flow electrophoresis for the separation of gamma globulin fraction from plasma. Combinations of these methods are used in the Cohn plasma fractionation process which is the major process by which plasma products are obtained.

Biological methods which employ the now-universal concept of biological specificity are the most recent techniques to be developed. Substrate binding involves the "lock and key" concept, and is exemplified by the specificity of the antigen-antibody reaction. Certain antigens and antibodies have been immobilized onto solid support systems and employed in treatment regimes and diagnosis in experimental animals and man. Protein A, derived from certain species of *Staphylococcus aureus*, binds to IgG and has also been used in macromolecular separation systems. Enzymes exhibit specific substrate reactivity and also have been immobilized, packaged into columns and used in experimental systems.

In many such systems, for instance when antibodies are coupled to solid surfaces, statistically one third of the binding sites are lost since coupling of one of the reactive arms results in concomitant loss of activity of that arm. Stereochemical considerations result in additional losses of binding sites resulting in overall losses of activity of as much as 50%. In addition to these problems, it is necessary to have a separate system for every immunospecific substance to be removed. That is, these systems are not universal in the sense that any immunospecifically recognizable component can be removed by a given system since only those substances which are specific for the bound antigen, antibody, protein, etc. are ultimately removed.

The various separation techniques described above can be further subdivided into off-line and on-line systems. Off-line systems include systems for commercial fractionation of donor plasma, exemplified by the aforementioned Cohn fractionation process, and new techniques such as polyethylene glycol precipitation of immune complexes and low temperature precipitation of cryoproteins. Off-line techniques are particularly useful when separation methods are slow, when there is a need to use toxic additives or when multiple steps in the separation process create difficult control situations.

On-line plasma treatment systems can be divided into three areas based on the degree of recycling involved. Plasma exchange techniques are those in which there is no plasma recycling. These separation techniques result in the separation of blood cells from plasma. Centrifuges in the form of cell separators are commonly used in this technique, along with the more recently developed membrane separation systems. One advantage of this separation technique is that the exact nature of the substance to be removed need not be known since all the plasma is removed. However, this technique requires total replacement of the plasma, and such replacement fluids are prohibitively expensive.

A partial plasma recycling system would involve the removal of a fraction, i.e. globulins, by precipitation, and would only require partial replacement of fluid and/or protein component. An advantage of the system would be a significant reduction in quantity and cost of replacement fluids.

Total plasma recycling involves specific removal of a target substance from the plasma while returning all remaining plasma components to the donor. Although such a system is highly desirable, it is generally applied in the treatment of disease and requires a precise knowledge of the pathogonesis of the disease and the rationale of the treatment.

A more sophisticated and elegant system would be a universal system in which biological fluids, such as whole blood or bone marrow, could be treated for selective removal of the target substance. Treatment of whole blood for selective removal of such substances would, however, require control of coagulation, platelet activation and related activation systems which may interfere with the filtration and/or selective removal of constituents from such biological fluids.

SUMMARY OF THE INVENTION

It has now been discovered in accordance with the present invention that immunospecifically recognizable dissolved or suspended substances may be selectively removed from solution by initially adding to the solution an immunospecific component which specifically reacts with the substance to form an immune complex. The immune complex so formed and immune complexes already present therein are thereafter removed from solution by contacting the solution with an adsorbent comprising non-immunospecific factor which exhibits an affinity for immune complexes.

According to the present invention, more particularly there is provided a method for selectively removing immunospecifically recognizable substances from biological fluids such as whole blood and bone marrow.

Hence, undesirable antigens or antibodies can be filtered from blood by first complexing the antigen or antibody with the corresponding complementary antibody or antigen. Immune complexes so formed or already present in the fluid being treated can then be passed by an adsorbent which exhibits an affinity for immune complexes. Non-immunospecific factors such as Clq, rheumatoid factor, Fc receptors or Fc receptor-bearing cells may be coupled to a solid phase to provide the adsorbent exhibiting affinity for immune complexes. The expression "Fc receptor or Fc receptor-bearing cells" is used herein to refer to those Fc receptor or Fc receptor-bearing cells that bind only to clustered or aggregated antibody, and not monomeric antibody. Thus, excluded from the scope of Fc receptor or Fc receptor-bearing cells, in the context of the present invention, are substances such as Protein A.

In accordance with another aspect of the present invention there is provided an apparatus for the selective removal from solution of any dissolved or suspended immune complex for which non-immunospecific factor exhibits an affinity. The apparatus comprises a chamber having therein a surface to which the non-immunospecific factor is bound. The apparatus has means for introducing the solution to be treated into the chamber whereby the solution is brought into contact with the surface having non-immunospecific factor bound thereon and means for discharging the treated solution from the chamber after adsorption of the immune complexes.

In addition to providing an efficient and effective way for selectively removing immunospecifically recognizable substances from solutions containing the same, the method and apparatus of the present invention possesses other notable advantages. First, the system is universal in that the method and apparatus is capable of removing all immunospecifically recognizable substances from solution without the need for modifying the adsorbent. This is due to the fact that the adsorbent, non-immunospecific factor bound to solid phase, exhibits an affinity for most immune complexes rather than any given immunospecifically-recognizable component thereof. Second, it has been found that adsorbed immune complexes can be retrieved, particularly in the case where Clq is used as an adsorbent component. Immune complexes can be readily desorbed from the adsorbent because the interaction between complexes and Clq is ionic-strength dependent. Third, as compared with the prior art plasma/blood filtration techniques, the need for expensive replacement fluids is obviated in practicing the present invention since only the target substance is removed, allowing the return of the treated or purified plasma/blood solution to its donor or elsewhere. Finally, the versatility of the present invention along with its universal nature provide a valuable diagnostic and research tool as well as providing a method and/or vehicle for treating a variety of diseases.

In another embodiment of the present invention, difficulties in the filtration of biological fluids, such as whole blood and bone marrow caused by various activation systems, such as the coagulation and platelet activation systems, have been overcome by suppression of the activation systems prior to treatment of the blood. Chelation of $Mg++$ and $Ca++$ ions is one way to deactivate these systems. Temperature reduction and/or preliminary removal of endogenous factors interfering with the binding of immune complex to non-immunospecific factor supplements suppression of the activation systems during filtration.

BRIEF DESCRIPTION OF THE DRAWINGS

The foregoing summary as well as the following detailed description of a preferred embodiment of the present invention will be better understood when read in conjunction with the accompanying drawings in which:

FIG. 1 is a flow diagram illustrating the process steps of the present invention in the removal of an immunospecifically recognizable substance from blood;

FIG. 2 is a perspective view showing the formation of a filter cartridge in accordance with the present invention;

FIG. 3 is a transverse sectional view taken along lines 3—3 of FIG. 2;

FIG. 4 is a longitudinal sectional view taken along lines 4—4 of FIG. 2 shown after the filter formation of the cartridge is completed and it is in place in a casing;

DETAILED DESCRIPTION OF THE INVENTION

Figures 5, 6, 7, 8:
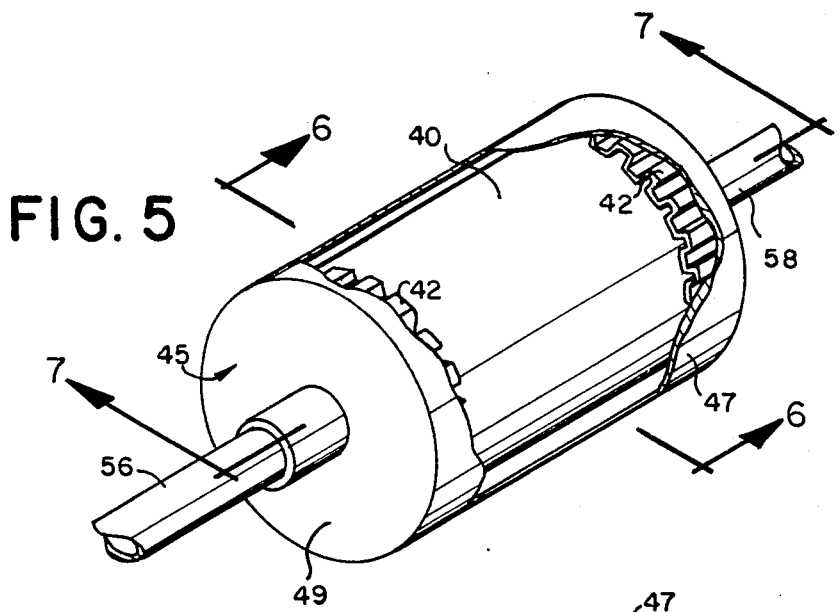
FIG. 5 is a perspective view of a second embodiment of a filter cartridge in a casing, with part of the casing broken away to show the cartridge.
FIG. 6 is a transverse sectional view taken along lines 6—6 of FIG. 5.
FIG. 7 is a longitudinal sectional view taken along lines 7—7 of FIG. 5.
FIG. 8 is a diagrammatic view showing non-immunospecific factor bound to a solid phase and showing adsorption of immune complexes from solution.

In accordance with the present invention, there is provided a method for selectively removing from a solution any dissolved or suspended immune complex present therein. Immune complexes already present in a solution, or immune complexes which are deliberately formed in order to remove a particular immunospecifically recognizable substance from the solution, may be removed in practicing the present invention.

The method comprises contacting the solution containing the immune complex, be it normally present therein or deliberately formed, with an adsorbent comprising non-immunospecific factor which exhibits an affinity for immune complexes for a time sufficient to substantially completely remove the immune complex out of solution.

In a preferred embodiment of the present invention, the adsorbent consists essentially of a solid phase having affixed thereon non-immunospecific factor and the contacting step comprises passing the solution containing immune complex into contact with the solid phase having non-immunospecific factor affixed thereon.

Since the present invention has application in the removal of immune complex from solution, it is therefore possible to selectively remove any immunospecifically-recognizable substance from a solution by adding to the solution the immunospecific component which reacts with the particular substance desired to be removed to form the immune complex. For example, if it is desirable to remove a particular antigen, the immunospecific component added to solution is the corresponding antibody which forms the immune complex which is thereafter adsorbed from the solution by passing the solution into contact with non-immunospecific factor bound to solid phase. Similarly, if it is desired to remove a particular antibody from the solution, the corresponding antigen is added to form the immune complex, which is likewise adsorbed.

Non-immunospecific factors used as an adsorbent in the present invention exhibit an affinity for most immune-complexed antibody. At least three kinds of non-immunospecific factor have the property of exhibiting an affinity for immune complex. They are: Clq (the antibody-binding portion of the first component of complement); rheumatoid factor; and Fc receptor or Fc receptor-bearing cells. Not all complexed antibodies however, are bound by non-immunospecific factors. For instance, with regard to Clq, not all antibodies are complement fixing. Non-complement-fixing antibodies, which in their complexed form are not adsorbed by Clq, can be modified by complexing them with a complement-fixing antibody such that the two antibodies (complement-fixing antibody and non-complement-fixing antibody) and the antigen which is ultimately to be removed, together make up an immune complex which will be adsorbed by Clq adsorbent. Similar modifications may be necessary when rhematoid factor, Fc receptors and Fc receptor-bearing cells are used as the adsorbent component.

It is known that these binding factors bind relatively weakly, or not at all, to uncomplexed antibody. FIG. 8 illustrates non-immunospecific factor bound to a solid phase and shows adsorption of immune complexes from solution. It is believed that when antibodies are clustered, via interaction with multivalent antigen, the affinity of these binding factors for immune complex is due to the opportunity for multiple interaction of complexed antibody with these non-immunospecific-binding factors. Alternatively, it is possible that the enhanced ability of these factors to bind to complexed antibody is due to a molecular reconfiguration within the complexed antibody which exposes the binding site on the antibody which is relatively specific for the non-immunospecific binding factors. Whichever mechanism is operative, it is possible to selectively remove from solution antigens or antibodies in their complexed form by contacting the naturally existing or performed immune complexes with bound non-immunospecific factor.

Hence, there is provided in accordance with the present invention, a universal method for selectively removing immune complexes from solutions whether alreadly present therein or specifically formed by first reacting the substance to be removed with its corresponding immunospecific component, by contacting the immune complex-bearing solution with the non-immunospecific adsorbent.

The present invention has particular application to the removal of immune complexes from biological solutions, and more specifically to intravascular solutions such as blood or bone marrow. A practical application of the present invention is in connection with the removal of intravascular fluid from a host. The removed fluid is thereafter treated according to the present invention to separate the immunospecifically-recognizable substance to be removed. The fluid, substantially free of such substance, is subsequently returned to the intravascular system of a host.

In the removal of immunospecifically recognizable substances from intravasular fluids, such as blood or bone marrow, it is necessary to defuse or suppress activation systems where required. For example, suppression of coagulation, complement and platelet activation systems is essential in the filtration of whole blood and bone marrow. Hence, in a preferred embodiment of the present invention, coagulation, and platelet activation systems are suppressed prior to the step of contacting the intravascular solution with non-immunospecific adsorbent. The suppression of cation-dependent activation systems, such as those mentioned above, is conveniently achieved by the addition of a chelating agent to the solution. Alternatively, or in conjunction with the addition of a chelating agent, lowering the temperature of blood or bone marrow to between about 5° C. and about 10° C. will suppress the activation systems. Reduction of temperature will also reduce the incidence of the phenomenon known as "capping". Capping is the process of redistribution of cell-surface determinants (immunospecifically recognizable) to one small part of the cell surface. When the substance to be removed is a cell, capping interferes with adsorption by non-immunospecific factor. It may also be desirable, when treating blood or bone marrow, to lower the level of endogenous factors normally present in the solution prior to contacting the solution with non-immunospecific adsorbent. In particular, any Clq, rheumatoid factor, Fc receptors or Fc receptor-bearing cells, which are normally present in blood and bone marrow, may interfere with the adsorption of immune complex by non-immunospecific factor, since these endogenous factors will necessarily be competing with the adsorbent for the binding sites on the immune complexes. Endogenous factors may be removed by techniques known to those skilled in the art.

Referring now to FIG. 1, there is shown a flow diagram illustrating the process steps of the present invention in the removal of an immunologically recognizable substance from whole blood. The steps, as illustrated, include suppression of the activation systems as well as a preliminary adsorption of endogenous factors which react with immune complexes. Thereafter, selective formation of immune complexes is achieved by adding to the blood an immunospecific component which specifically reacts with the substance to be removed to form an immune complex. The blood containing preformed immune complex and any immune complex already present therein is thereafter contacted with an adsorbent comprising non-immunospecific factor bound to a solid phase, which non-immunospecific factor exhibits an affinity for immune complex and thereby adsorbs from the blood immune complexes present therein.

It will be appreciated by those skilled in the art that the present invention has application to the removal and retrieval (when desired) from blood of: (a) specific autologous or heterologous proteins and other macromolecules or complexes thereof; (b) specific antibodies; (c) specific cells or cell subsets; and (d) drugs, drug-macromolecular complexes or drug metabolites. In practicing the present invention where the intravascular solution is a bone marrow suspension, it is also possible to selectively remove malignant cells therefrom or cell subsets or precursor cells. In addition, the present invention could find use in cell sorting—the collection and isolation of specific cells. It will be appreciated by those skilled in the art that the present invention has clinical application in conjunction with plasmapheresis (the separation of red blood cells from the plasma of a blood donor and the subsequent return of the blood cells to the donor's circulatory system) or could be used for hemoperfusion directly.

In accordance with another embodiment of the present invention, immune complexes which are adsorbed out of the solution may be separated from the adsorbent by isolating the adsorbent from the solution and desorbing the immune complex bound to the non-immunospecific factor. In the case where Clq is the adsorbent, immune complexes adsorbed can be readily desorbed because the interaction between immune complexes and Clq is ionic-strength dependent. Hence, by increasing the salt content, or alternatively, by the addition of one or more of a variety of diamino alkyl compounds, e.g., diaminobutane, the immune complexes readily desorb. This embodiment is of particular significance when using the method of the present invention for cell sorting.

There are substances which can be immunospecifically recognized but which will not form complexes of the type which will be readily adsorbed by Clq, rheumatoid factor, Fc receptors or Fc receptor-bearing cells. Such substances are generally monovalent with respect to antigenic determinents (hapten-like) and can be removed from solution in the following fashion. The immunospecific component which specifically reacts with the hapten-like substance comprises two constituents. The first constituent is one which is not capable by itself, of forming with the substance to be removed an immune complex that can be readily adsorbed by the non-immunospecific factor. The second constituent is one which specifically binds to the first constituent and forms, with the first constituent and the substance to be removed, an immune complex which is adsorbed by non-immunospecific factor. The added component, comprising the first and second constituent, comes out of the solution along with the substance to be removed. For example, in a solution containing dinitrophenol (DNP) as the hapten-like substance to be removed, an immune complex formed from anti-DNP (of mouse origin) and purified goat anti-mouse, i.e., immune complex formed between these two antibodies, is added to the solution. In a solution containing DNP, the complexed mouse antibody removes the DNP out of solution because the complex contains antibodies specific for it. The mouse/goat antibody-DNP complex is itself an immune complex which is thereby adsorbed from the solution by non-immunospecific adsorbent. The addition of complexed mouse/goat antibodies, when bound to the substance desired to remove, may provide the additional binding sites to which the non-immunospecific factor can bind. This approach may prove useful for retrieving cells having only a few antigenic determinants which may be insufficient to give adequate binding to Clq/rheumatoid-like adsorbents.

In accordance with the present invention, there is provided a novel apparatus for the selective removal from a carrier solution of dissolved or suspended immune complex which can be adsorbed by non-immunospecific factor. Referring to FIGS. 2-4 of the drawings, the apparatus comprises means forming a chamber, means defining a surface in the chamber having non-immunospecific factor bound thereon, means for introducing the carrier solution having the dissolved or suspended immune complex present therein into contact with surface means having non-immunospecific factor bound thereon to remove immune complex from the solution, and discharging means for discharging the carrier solution from said chamber after removal of immune complex from the carrier solution.

In a preferred embodiment of the apparatus, as shown in FIGS. 2 and 3, the chamber comprises a helically-wound sheet 20 having opposite surfaces for receiving the non-immunospecific factor, and spaced-apart spacer means 22 between the helical convolutions of the sheet which is wound on a hollow, cylindrical perforate core member 26. For the purposes of illustration the thickness of the sheet is greatly enlarged. As shown in FIG. 4, the chamber in this arrangement is formed between the spaced-apart spacer means 22 and the confronting surfaces of the adjacent convolutions of sheet 20. The sheet may be of any material which will bind non-immunospecific factor. A preferred material when Clq is the factor is polystyrene since it binds Clq without interfering with Clq-immune complex reactive sites.

As illustrated in FIGS. 2 and 3, the spacer means 22 comprise strips of material, such as Teflon ® tape (or other polytetrafluoroethylene materials) which are impervious to the solution being treated. As illustrated in FIG. 4, sheet material 20 and spacers 22 which are helically-wound on perforate core member 26 form a cartridge which is housed in a cylindrical housing 25 having an annular space formed between cylindrical perforate core member 26 and an outer perforate cylindrical wall 27. One end of the annular space is closed by a radial wall 28, which is imperforate and also closes one end of cylindrical housing 25.

Means is provided to cause carrier solution to flow through the filter chamber formed by the sheet material 20 and the spacers 22. In the present embodiment introducing means comprises an inlet 16 and discharging means comprise an outlet 18 which affords communication with the chamber means between strips 22 for introducing and discharging the carrier solution. The solution enters through inlet means 16 under pressure into the interior of the cylindrical core member 26 and is forced through openings 30 such that the solution flows into the space between the first two convolutions on the inside of the cartridge, and then circumferentially along the helical convolutions of sheet 20. After passage through the complete helical path between the convolutions, it passes out between the last two convolutions on the outside of the cartridge, through perforate wall 27 and thereafter through outlet means 18, as indicated by the arrows in FIG. 4.

As illustrated in FIG. 4, the housing 25 is enclosed in a cylindrical casing 32. Cylindrical casing 32 serves to contain the cartridge and its housing and operates in conjunction with introducing means and discharging means to allow the solution being treated for removal of immunospecifically recognizable substances in the form of immune complexes to pass into contact with non-immunospecific factor bound to sheet 20. The flow path of the solution in the filter chamber has a flow area determined by the cross-section of the filter chamber longitudinally of the cartridge and a length corresponding to the length of the sheet 20 wound helically on the core 26.

In another embodiment of the apparatus of the present invention, as illustrated in FIGS. 5-7, spacer means 42 comprise corrugated strips of material which have crests and valleys with alternating runs therebetween. As in the previous embodiment of the apparatus, the chamber comprises a sheet 40 helically wound about a cylindrical core member 46, which is closed at either end. The sheet 40 similarly has opposite surfaces for receiving non-immunospecific factor. As shown in FIGS. 6-7 the chamber is formed between spaced-apart spacer means 42 and the confronting surfaces of the adjacent convolutions of sheet 40. However, in this arrangement, the flow of the solution is primarily axial rather than circumferential, as indicated by the arrows in FIG. 7, so that the solution flows through corrugated strips 42 between adjacent convolutions of sheet 40.

As illustrated in FIGS. 6-7, the spacer means 42 comprise corrugated strips of material, such as moldable plastic. As illustrated in FIG. 7, the helically-wound sheet material 40 wound about core member 46 and corrugated strips 42 froms a cartridge which is housed in a cylindrical casing 45 having an annular space formed between the core member 46 and an outer imperforate cylindrical wall or shell of the casing 47. Both ends of the outer wall shell 47 are closed by radial walls 49 which are also imperforate and prevent escape of the carrier solution therethrough.

Means is provided to cause the carrier solution to flow axially through the filter chamber formed by sheet material 40 and corrugated spacers 42. In the present embodiment introducing means comprise an inlet 56 and discharging means comprise an outlet 58 which afford communication with the chamber means through corrugated strips 42 along the convoluted surfaces of sheet 40 for introducing and discharging the carrier solution. To this end, as illustrated in FIG. 7 the radial walls 49 are spaced from the opposite ends of the cartridge formed by the core 46, sheet material 40 and spacers 42, to provide clearance spaces 50 adjacent the inlet 56 and outlet 58. Thus, the solution enters through inlet 56 under pressure and flows into the space 50 provided between the wall 49 and the filter cartridge. The solution is thereafter forced through the corrugated strips 42 adjacent inlet 56, flowing axially through alternating runs of the corrugation into the filter chamber. At the other end, the solution passes out through the corrugated strip 42 adjacent the outlet 58, into the clearance space 50 at that end, allowing discharge of the treated solution from the cartridge through outlet 58.

As illustrated in FIGS. 5 and 7, the cylindrical casing 45 serves to contain and house the cartridge formed from core member 46, helically-wound sheet 40 and corrugated spacer means 42 as in the previous embodiment. The cyclindrical casing 45 operates in conjunction with introducing means and discharging means to allow the solution being treated to pass into contact with non-immunospecific factor bound to sheet 40.

In a modification of this embodiment the sheet material may itself be molded to form a corrugated sheet of material which is then helically wound about the core member to form the filter cartridge. This modification obviates the need for corrugated spacer strips of material per se, however, it may desirable to have spaced-apart strips of material to avoid nesting of adjacent convolutions of the corrugated sheet. In addition, providing a pre-molded corrugated sheet of material serves to increase the surface area over which the carrier solution flows and thereby greatly enhances contact with non-immunospecific factor bound to the sheet. In this second embodiment of the invention, including the modification described above, the flow path of the solution in the chamber has a flow area only slightly less than the transverse cross-section of the annular space between the core 46 and the shell 47, and a length corresponding to the axial length of the cartridge.

The invention will be further understood by reference to the following examples, which are intended to illustrate, and not to limit the invention.

EXAMPLE 1

An apparatus for the removal of immunospecifically recognizable substances from a solution is constructed using a plastic core cylinder having perforations or openings thereabout with dimensions 20 cm high × 10 cm in diameter, a sheet of polystyrene with non-immunospecific factor bound thereto with dimensions 10 cm wide × 5 mils (0.1 mm) thick × variable length, and 2 pieces of Teflon ® tape (or other PTFE material) with dimensions 1 cm wide × 0.1 cm thick × same length as sheet, and a second perforated shell cylinder 20 cm high × 12 cm in diameter, as follows. The 10 cm wide side of the polystyrene sheet is affixed to the surface of the core cylinder (aligned along the cylindrical axis) such that it can be rolled around the cylinder. Prior to rolling, the Teflon ® tape (or other PTFE material) is affixed to the cylinder so that the tape will lie on top of the edges of the long sides of the plastic sheet. By rolling the cylinder in this fashion, a spiral cross section results where adjacent parts of the polystyrene form a chamber 8 cm wide and 0.1 cm high and of a length determined by the length of the tapes and polystyrene sheets rolled around the cylinder until the diameter corresponds to the interior diameter of the shell cylinder. It is then inserted in the shell cylinder and an end wall is bonded to the inner and outer cylinder to close one end to form a filter cartridge. This arrangement allows both sides of the polystyrene sheet to be used as an adsorbent. The shelled cartridge thus formed is encapsulated in a casing so that an inlet communicates with the inside of the cartridge and the outlet communicates with the outside so as to permit passage of the solution through the chamber.

EXAMPLE 2

Removal of an immunospecifically recognizable substance, such as antigen, from solution is accomplished by adding to the solution an antibody which is specific for the antigen to be removed. The antibody is added in limited amounts such that the antigen to be removed is in "determinant" excess. This accomplishes two things: (1) limited amounts of antibody are used and (2) the complex of antibody and antigen remains soluble. The solution is thereafter passed through the apparatus described in Example 1 which substantially completely removes immune complexes thus formed or already present in the solution.

As those skilled in the art will appreciate, the present invention provides a very effective and efficient way of removing immunospecifically recognizable substances from solution, and in the case of biological fluids, allows for the recycling and return of the fluid to the donor host.

While the method and apparatus herein described constitute a preferred embodiment of the invention, it is to be understood that the invention is not limited to the precise embodiment of the described method and apparatus, but that changes may be made therein without departing from the spirit and scope of the invention, as set forth in the appended claims.

We claim:

1. A method for selectively removing from a solution any soluble or suspended immunospecifically recognizable substance, which method comprises the steps of:
   a. determining the amount of said substance present in said solution;

b. adding to said solution an immunospecific component capable of reacting specifically with said substance, said component being added in a quantity appropriate to form immune complexes with the amount of said substance determined to be present in said solution, said immune complexes being capable of binding to non-immunospecific factor having an affinity therefor; and c. contacting said solution with an adsorbent comprising non-immunospecific factor which exhibits an affinity for said immune complexes, whereby said immune complexes become bound to said non-immunospecific factor and said immunospecifically recognizable substance is substantially completely removed from said solution.

2. A method according to claim 1, wherein said substance to be removed from said solution is an antigen and said immunospecific component added to said solution to form said immune complex is the corresponding antibody specific to said antigen.

3. A method according to claim 1, wherein said substance to be removed from said solution is an antibody and said immunospecific component added to said solution to form said immune complex is the corresponding antigen specific to said antibody.

4. The method according to claim 1, wherein said adding immunospecific component comprises a first constituent which is not capable of forming with said substance an immune complex which can be readily adsorbed by said non-immunospecific factor, and a second constituent which binds to said first constituent, and forms with said first constituent and said substance an immune complex which can be adsorbed by said non-immune specific factor, whereby said added component is removed out of said solution with said substance.

5. The method according to claim 1, wherein said non-immunospecific factor is selected from the group consisting of Clq, rheumatoid factor and Fc receptor or Fc receptor-bearing cells, said Fc receptor or Fc receptor-bearing cells being characterized by a binding affinity for aggregated antibody, and not for monomeric antibody.

6. A method according to claim 1, wherein said non-immunospecific factor is Fc receptor or Fc receptor-bearing cells, said Fc receptor or Fc receptor-bearing cells being characterized by a binding affinity for aggregated antibody, and not for monomeric antibody.

7. A method according to claim 1, wherein said immunospecifically recognizable substance is a cell having antigenic reactive sites associated therewith and said immunospecific component added to said solution to form said immune complexes is antibody which reacts specifically with said antigenic reactive sites.

8. A process according to claim 1, wherein the temperature of the solution is between about 5° C. and about 10° C.

9. A method according to claim 1, wherein said adsorbent consists essentially of a solid phase having affixed thereon said non-immunospecific factor, and said contacting step comprises passing said solution containing said immune complex into contact with said solid phase having said non-immunospecific factor affixed thereon.

10. The method according to claim 9, including the additional step of separating said complex from said adsorbent by isolating said adsorbent from said solution and desorbing said immune complex bound to said non-immunospecific factor.

11. The method according to claim 1, wherein said solution is biological fluid.

12. The method according to claim 11, wherein said biological fluid comprises intravascular fluid derived from a host.

13. The method according to claim 12, wherein said intravascular fluid substantially completely free of said immune complex is returned to the intravascular system of said host.

14. The method according to claim 12, wherein said intravascular fluid comprises bone marrow.

15. The method according to claim 12, wherein said intravascular fluid comprises blood.

16. The method according to claim 15, including the additional step of lowering the levels of endogenous factors which react with said immune complexes prior to said step of contacting said solution with said adsorbent.

17. The method according to claim 16, wherein said endogenous factors whose levels are lowered are selected from the group consisting of Clq, rheumatoid factor and Fc receptors or Fc receptor-bearing cells.

18. The method according to claim 15, including the additional step of suppressing coagulation, complement and platelet activation systems prior to said step of contacting said solution with said adsorbent for adsorption of said immune complexes.

19. The method according to claim 18, wherein said systems are suppressed by adding a chelating agent to said intravascular fluid in an amount sufficient to effect the chelation of calcium and magnesium ions present therein.

20. The method according to claim 18, wherein said systems are suppressed by cooling said intravascular fluid to about 5° C. to about 10° C.

* * * * *